US010841626B2

(12) United States Patent
Raju et al.

(10) Patent No.: US 10,841,626 B2
(45) Date of Patent: Nov. 17, 2020

(54) SELECTIVE PICTURE-BASED ENCRYPTION OF VIDEO STREAMS

(71) Applicant: Texas Instruments Incorporated, Dallas, TX (US)

(72) Inventors: Veeramanikandan Raju, Bangalore (IN); Madhukar Budagavi, Plano, TX (US)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 0 days.

(21) Appl. No.: 14/525,197

(22) Filed: Oct. 27, 2014

(65) Prior Publication Data

US 2016/0119660 A1 Apr. 28, 2016

(51) Int. Cl.
*H04N 21/2347* (2011.01)
*H04N 21/234* (2011.01)
*H04N 21/845* (2011.01)

(52) U.S. Cl.
CPC ..... *H04N 21/23476* (2013.01); *H04N 21/234* (2013.01); *H04N 21/8456* (2013.01)

(58) Field of Classification Search
CPC .. H04N 19/00; H04N 19/114; H04N 21/2347; H04N 21/23476; H04N 21/234; H04N 21/23473; H04N 21/43856; H04N 19/167; H04N 19/40; H04N 19/517; H04N 21/8456
See application file for complete search history.

(56) References Cited

U.S. PATENT DOCUMENTS 6,519,340 B1 * 2/2003 Javidi ...................... H04K 1/00 348/E7.056
6,804,294 B1 * 10/2004 Hartung ................. H04N 19/52 375/240
7,058,177 B1 * 6/2006 Trimberger ........... H04L 9/0637 380/28
7,320,069 B1 * 1/2008 Sundharraj ............. G06F 21/10 348/E7.056
8,401,188 B1 * 3/2013 Swaminathan ......... G06F 21/10 380/200
2002/0090027 A1 * 7/2002 Karczewicz ..... H04N 21/23406 375/240.01
2002/0196939 A1 * 12/2002 Unger .................... H04N 7/162 380/216
2003/0152226 A1 * 8/2003 Candelore ................ H04K 1/00 380/218
2003/0231767 A1 * 12/2003 Carbajal ............. H04L 63/0428 380/200
2004/0037421 A1 * 2/2004 Truman ............... H04N 7/1675 380/200

(Continued)

OTHER PUBLICATIONS

S.Rajagopal, Partial Video Encryption Using Random Permutation Based on Modification on Dct Based Transformation, 2013.*

(Continued)

*Primary Examiner* — Huan V Doan

(74) *Attorney, Agent, or Firm* — Ebby Abraham; Charles A. Brill; Frank D. Cimino

(57) ABSTRACT

A method for encrypting a video stream in a video encoder is provided that includes receiving the video stream and encrypting randomly selected pictures in the video stream as the video stream is encoded.

13 Claims, 6 Drawing Sheets

(56) References Cited

U.S. PATENT DOCUMENTS

| | | | | |
|---|---|---|---|---|
| 2004/0081333 A1* | 4/2004 | Grab | H04K 1/00 | 382/100 |
| 2004/0193871 A1* | 9/2004 | Seshadri | H04L 63/0428 | 713/154 |
| 2005/0094809 A1* | 5/2005 | Pedlow, Jr. | H04N 21/2365 | 380/200 |
| 2006/0140270 A1* | 6/2006 | Li | H04N 19/159 | 375/240.12 |
| 2007/0116277 A1* | 5/2007 | Ro | H04N 7/167 | 380/201 |
| 2007/0160208 A1* | 7/2007 | MacLean | H04N 7/1675 | 380/210 |
| 2010/0005483 A1* | 1/2010 | Rao | H04N 7/17318 | 725/25 |
| 2011/0064129 A1* | 3/2011 | Bennett | H04N 19/172 | 375/240.01 |
| 2011/0064220 A1 | 3/2011 | Chen et al. | | |
| 2011/0123023 A1* | 5/2011 | Choi | H04N 21/2347 | 380/200 |
| 2013/0039411 A1* | 2/2013 | Aoki | H04N 19/61 | 375/240.03 |
| 2013/0156186 A1* | 6/2013 | Candelore | H04N 7/1675 | 380/210 |
| 2015/0033008 A1* | 1/2015 | Einarsson | H04L 63/0428 | 713/150 |

OTHER PUBLICATIONS

Rajagopal et al, Partial Video Encryption Using Random Permutation Based on Modification on Dct Based Transformation, Jun. 2013, IRJES, vol. 2, 5 pages.*

Yeung et al., Partial Video Encryption based on Alternating Transforms, IEEE, 4 pages (Year: 2009).*

Cheng et al., Partial Encryption of Compressed Images and Videos, IEEE, 13 pages (Year: 2000).*

Heinz Hofbauer et al, "Transparent Encryption for HEVC Using Bit-Stream-Based Selective Coefficient Sign Encryption", 2014 IEEE International Conference on Acoustics, Speech and Signal Processing (ICASSP), May 4-9, 2014, Florence, Italy, pp. 1986-1990.

Marc Van Droogenbroeck and Raphael Benedett, "Techniques for a Selective Encryption of Uncompressed and Compressed Images", Proceedings of ACIVS 2002 (Advanced Concepts for Intelligent Vision Systems), Sep. 9-11, 2002, Ghent, Belgium, pp. 90-97.

M. Abomhara et al, "Enhancing Selective Encryption for H.264/AVC Using Advanced Encryption Standard", International Journal of Computer Theory and Engineering, vol. 2, No. 2, Apr. 2010, pp. 223-229.

Pranay Meshram et al, "Comparative Study of Selective Encryption Algorithm for Wireless Adhoc Network", International Journal of Research in Engineering & Applied Sciences, vol. 2, Issue 2, Feb. 2012, pp. 506-517.

A. Massoudi et al, "Overview on Selective Encryption of Image and Video: Challenges and Perspectives", EURASIP Journal on Information Security, vol. 2008, Article ID 179290, pp. 1-18.

Xiliang Liu and Ahmet M. Eskicioglu, "Selective Encryption of Multimedia Content in Distribution Networks: Challenges and New Directions", IASTED Communications, Internet & Information Technology (CIIT), Nov. 2003, Scottsdale, Arizona, pp. 527-533.

Yogita Negi, "A Survey on Video Encryption Techniques", International Journal of Emerging Technology and Advanced Engineering, vol. 3, Issue 4, Apr. 2013, pp. 234-237.

Benjamin Bross et al, High Efficiency Video Coding (HEVC) Text Specification Draft 10 (for FDIS & Last Call), JCTVC-L1003_v34, Joint Collaboration Team on Video Coding (JCT-VC) of ITU-T SG 16 WP 3 and ISO/IEC JTC 1/S 29/WG 11, pp. 1-298, Jan. 14-23, 2013, Geneva, Switzerland.

Salah Aly, "A Light-Weight Encrypting for Real Time Video Transmission", CTI Symposium Conference, DePaul University, Chicago, USA, Nov. 2003, pp. 1-10.

Thomas Stutz and Andreas Uhl, "A Survey of H.264 AVC/SVC Encryption", IEEE Transactions on Circuits and Systems for Video Technology, vol. 22, No. 3, Mar. 2012, pp. 325-339.

"TMS320DM6467 Digital Media System-on-Chip", SPRS403G, Texas Instruments Incorporated, Dec. 2007, revised Oct. 2010, pp. 1-355.

Z. Shahid et al, "Fast Protection of H.264/AVC by Selective Encryption of CAVLC and CABAC for I & P Frames", Journal of IEEE Transactions on Circuits and Systems for Video Technology, vol. 21, Issue 5, Mar. 2011, pp. 1-17.

Pavithra. C and Vinod. B. Durdi, "Analization and Comparison of Selective Encryption Algorithms with Full Encryption for Wireless Networks", International Journal of Engineering Trends and Technology (IJETI), vol. 4, Issue 5, May 2013, pp. 2083-2088.

* cited by examiner

SELECTIVE PICTURE-BASED ENCRYPTION OF VIDEO STREAMS

BACKGROUND OF THE INVENTION

Field of the Invention

Embodiments of the present invention generally relate to encryption in video coding, and more specifically relate to selective picture-based encryption of video streams.

Description of the Related Art

Conventionally, video content providers wishing to protect their video content have elected to encrypt all the data associated with the video content before streaming the content over a network. This approach consumes considerable computational resources both for the content provider and for the recipients of the encrypted video content as each recipient is required to decrypt the video data. Accordingly, improvements in the encryption of video streams that reduce computational resource consumption for both the provider and the recipient of video streams are desirable.

SUMMARY

Embodiments of the present invention relate to methods, apparatus, and computer readable media for selective picture-based encryption of video streams as the video streams are encoded. In one aspect, a method for encrypting a video stream in a video encoder is provided that includes receiving the video stream and encrypting randomly selected pictures in the video stream as the video stream is encoded.

In one aspect, an apparatus configured to encode a video stream is provided that includes means for receiving the video stream, and means for encrypting randomly selected pictures in the video stream as the video stream is encoded.

BRIEF DESCRIPTION OF THE DRAWINGS

Particular embodiments will now be described, by way of example only, and with reference to the accompanying drawings.

DETAILED DESCRIPTION OF EMBODIMENTS OF THE INVENTION

Figure 1:
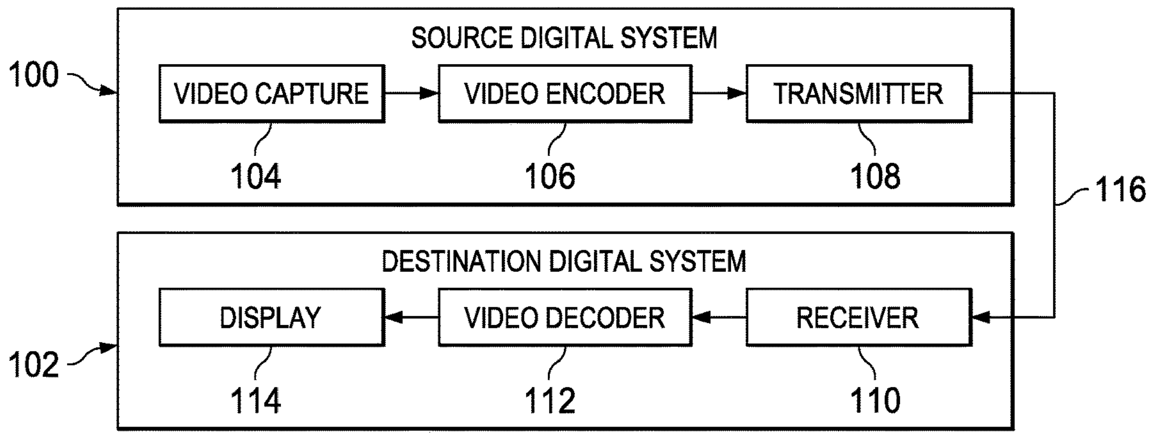
FIG. 1 is a block diagram of a digital system.

Specific embodiments of the invention will now be described in detail with reference to the accompanying figures. Like elements in the various figures are denoted by like reference numerals for consistency.

As used herein, the term "picture" may refer to a frame or a field of a frame. A frame is a complete image captured during a known time interval.

Embodiments of the invention provide for selective picture-based encryption of a video stream as the video stream is encoded. In some embodiments, randomly selected subsets of pictures in sequences of pictures (picture groups) of the video stream are encrypted as the video stream is encoded. That is, the video stream is logically divided into groups of sequential pictures, and within a given picture group, a subset of randomly selected pictures is encrypted. The number of pictures in a picture group and the number of randomly selected pictures in a picture group to be encrypted may be based on the picture rate of the incoming video stream.

The Joint Collaborative Team on Video Coding (JCT-VC) of ITU-T WP3/16 and ISO/IEC JTC 1/SC 29/WG 11 has recently released the first version of the next-generation video coding standard referred to as High Efficiency Video Coding (HEVC). HEVC version 1 is described in B. Bross, et al., "High Efficiency Video Coding (HEVC) Text Specification Draft 10 (for FDIS & Last Call)," JCTVC-L1003_v34, Joint Collaborative Team on Video Coding (JCT-VC) of ITU-T SG16 WP3 and ISO/IEC JTC1/SC29/WG1, Geneva, CH, Jan. 14-23, 2013, which is incorporated by reference herein in its entirety. For convenience of description, embodiments are described herein in reference to HEVC. One of ordinary skill in the art will understand that embodiments of the invention are not limited to HEVC.

Similar to previous video coding standards such as H.264/AVC, HEVC is based on a hybrid coding scheme using block-based prediction and transform coding. First, the input signal is split into rectangular blocks that are predicted from the previously decoded data by either motion compensated (inter) prediction or intra prediction. The resulting prediction error is coded by applying block transforms based on an integer approximation of the discrete cosine transform, which is followed by quantization and coding of the transform coefficients.

In HEVC, a largest coding unit (LCU) is the base unit used for block-based coding. A picture is divided into non-overlapping LCUs. That is, an LCU plays a similar role in coding as the macroblock of H.264/AVC, but it may be larger, e.g., 32×32, 64×64, etc. An LCU may be partitioned into coding units (CU). A CU is a block of pixels within an LCU and the CUs within an LCU may be of different sizes. The partitioning is a recursive quadtree partitioning. The quadtree is split according to various criteria until a leaf is reached, which is referred to as the coding node or coding unit. The maximum hierarchical depth of the quadtree is determined by the size of the smallest CU (SCU) permitted. The coding node is the root node of two trees, a prediction tree and a transform tree. A prediction tree specifies the position and size of prediction units (PU) for a coding unit. A transform tree specifies the position and size of transform units (TU) for a coding unit. A transform unit may not be larger than a coding unit and the size of a transform unit may be, for example, 4×4, 8×8, 16×16, and 32×32. The sizes of the transforms units and prediction units for a CU are determined by the video encoder during prediction based on minimization of rate/distortion costs.

FIG. 1 shows a block diagram of a digital system that includes a source digital system 100 that transmits encoded video streams to a destination digital system 102 via a communication channel 116. The source digital system 100 includes a video capture component 104, a video encoder component 106, and a transmitter component 108. The video capture component 104 is configured to provide a video stream to be encoded by the video encoder component 106. The video capture component 104 may be, for example, a video camera, a video archive, or a video feed from a video content provider. In some embodiments, the video capture component 104 may generate computer graphics as the video stream, or a combination of live video, archived video, and/or computer-generated video.

The video encoder component 106 receives a video stream from the video capture component 104 and encodes it for transmission by the transmitter component 108. The video encoder component 106 receives the video stream from the video capture component 104 as a sequence of pictures, divides the pictures into largest coding units (LCUs), and encodes the video data in the LCUs. The video encoder component 106 may be configured to perform selective picture-based encryption as described herein during the encoding process. An embodiment of the video encoder component 106 is described in more detail herein in reference to FIGS. 2A and 2B.

The transmitter component 108 transmits the encoded video data to the destination digital system 102 via the communication channel 116. The communication channel 116 may be any communication medium, or combination of communication media suitable for transmission of the encoded video stream, such as, for example, wired or wireless communication media, a local area network, or a wide area network.

The destination digital system 102 includes a receiver component 110, a video decoder component 112 and a display component 114. The receiver component 110 receives the encoded video data from the source digital system 100 via the communication channel 116 and provides the encoded video data to the video decoder component 112 for decoding. The video decoder component 112 reverses the encoding process performed by the video encoder component 106 to reconstruct the LCUs of the video stream. The video decoder component 112 may be configured to decrypt, as part of the decoding process, the pictures of the video data encrypted by the video encoder component 106 using selective picture-based encryption. An embodiment of the video decoder component 112 is described in more detail below in reference to FIGS. 3A and 3B.

The reconstructed video stream is displayed on the display component 114. The display component 114 may be any suitable display device such as, for example, a plasma display, a liquid crystal display (LCD), a light emitting diode (LED) display, etc.

In some embodiments, the source digital system 100 may also include a receiver component and a video decoder component and/or the destination digital system 102 may include a transmitter component and a video encoder component for transmission of video streams both directions for video streaming, video broadcasting, and video telephony. Further, the video encoder component 106 and the video decoder component 112 may perform encoding and decoding in accordance with one or more video compression standards. The video encoder component 106 and the video decoder component 112 may be implemented in any suitable combination of software, firmware, and hardware, such as, for example, one or more digital signal processors (DSPs), microprocessors, discrete logic, application specific integrated circuits (ASICs), field-programmable gate arrays (FPGAs), etc.

Figure 2A:
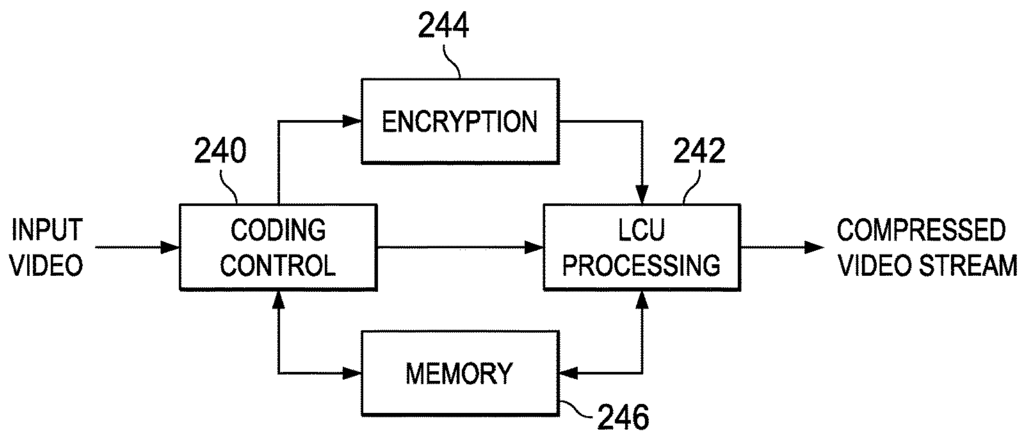
FIGS. 2A and 2B are block diagrams of an example video encoder.
Figure 2B:
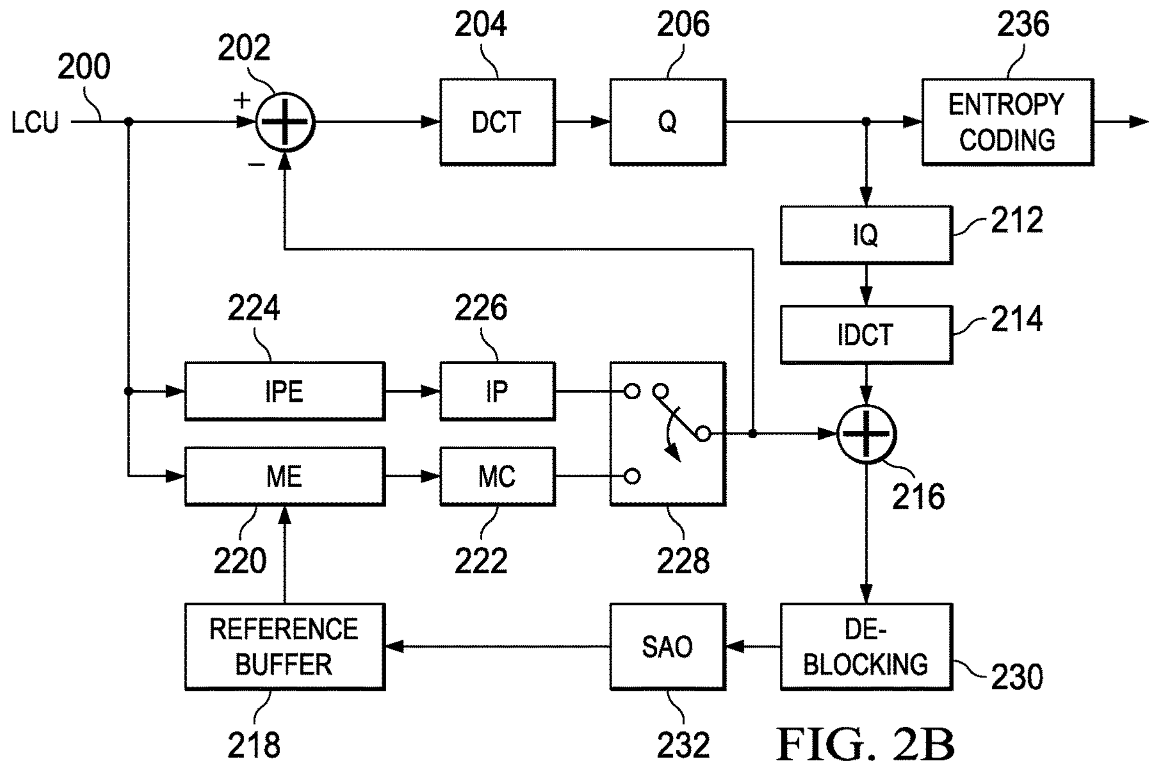

FIGS. 2A and 2B show block diagrams of an example video encoder, e.g., the video encoder component 106 of FIG. 1, configured to perform selective picture-based encryption as described herein during the encoding process. FIG. 2A shows a high level block diagram of the video encoder and FIG. 2B shows a block diagram of the LCU processing component 242 of the video encoder. As shown in FIG. 2A, the video encoder includes a coding control component 240, an LCU processing component 242, an encryption component 244, and a memory 246. The memory 246 may be internal (on-chip) memory, external (off-chip) memory, or a combination thereof. The memory 246 may be used to communicate information between the various components of the video encoder.

The coding control component 240 sequences the various operations of the video encoder, i.e., the coding control component 240 runs the main control loop for video encoding. For example, the coding control component 240 performs processing on the input video stream that is to be done at the picture level, such as determining the coding type (I, P, or B) of a picture based on a high level coding structure, e.g., IPPP, IBBP, hierarchical-B, and dividing a picture into LCUs for further processing.

In addition, for pipelined architectures in which multiple LCUs may be processed concurrently in different components of the LCU processing, the coding control component 240 controls the processing of the LCUs by various components of the LCU processing component 242 in a pipeline fashion. For example, in many embedded systems supporting video processing, there may be one master processor and one or more slave processing modules, e.g., hardware accelerators. The master processor operates as the coding control component and runs the main control loop for video encoding, and the slave processing modules are employed to off load certain compute-intensive tasks of video encoding such as motion estimation, motion compensation, intra prediction mode estimation, transformation and quantization, entropy coding, and loop filtering. The slave processing modules are controlled in a pipeline fashion by the master processor such that the slave processing modules operate on different LCUs of a picture at any given time. That is, the slave processing modules are executed in parallel, each processing its respective LCU while data movement from one processor to another is serial.

Further, the coding control component 240 performs the processing for picture-based selective encryption as described herein, passing any pictures to be encrypted to the encryption component 244. More specifically, the coding control component 240 randomly selects the pictures to be encrypted, using any suitable technique for random picture selection. For example, the coding control component may perform the operations of the methods of FIGS. 4-6 to implement picture-based selective encryption as a video stream is encoded. In some embodiments, the selected pictures are encrypted prior to encoding. In some embodiments, the selected pictures are encrypted after encoding. In some embodiments, the coding control component 240 causes the video stream encoding to be lossless.

Figure 3A:
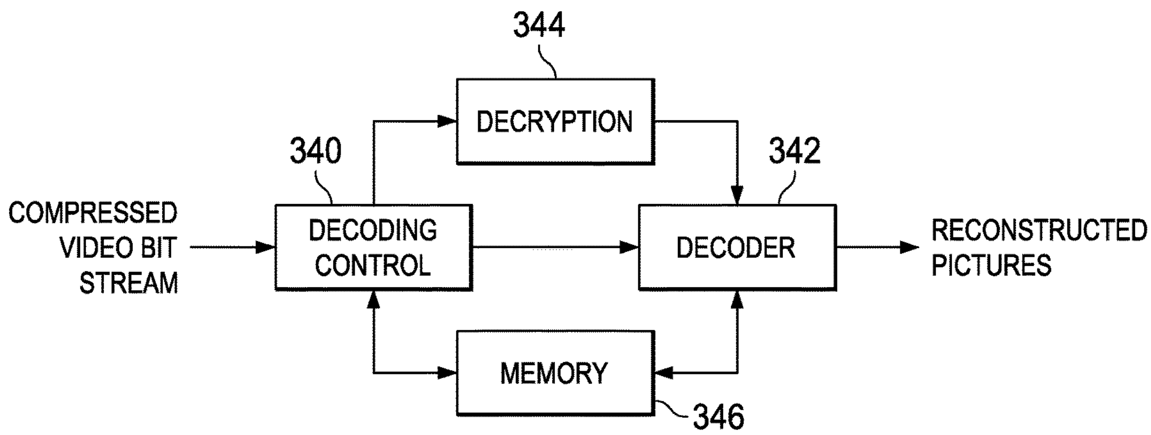
FIGS. 3A and 3B are block diagrams of an example video decoder.
Figure 3B:
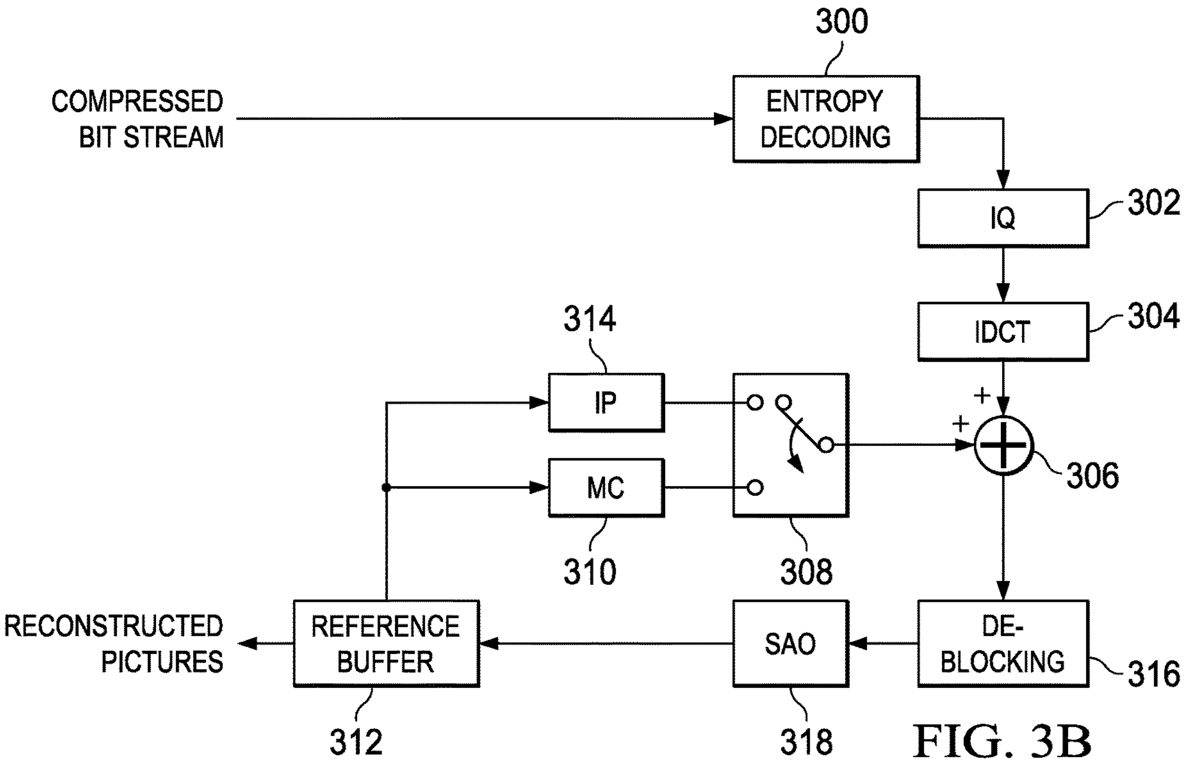

The coding control component 240 also performs processing needed to communicate to a decoder, e.g., the decoder of FIGS. 3A and 3B, receiving the encoded bit stream which of the pictures is encrypted and any other information needed to decrypt the encrypted pictures, e.g., a key or keys for decryption and/or the type of encryption used. This information may be communicated in any suitable way, e.g., in one or more supplemental enhancement information (SEI) messages, in suitable headers and/or parameter sets, etc.

The encryption component 344 performs the encryption of the pictures selected by the coding control component 240. The encryption component 344 may use any suitable encryption technique. Examples of suitable techniques include byte permutation algorithms, pure permutation algorithms in which the bytes are scrambled, zig-zag permutation algorithms that map individual blocks to a vector using a random permutation list (secret key), etc. Some suitable techniques are described in M. Abomhara, et al., "An Overview of Video Encryption Techniques," International Journal of Computer Theory and Engineering, Vol. 2, No. 1, February, 2010, pp. 103-110.

FIG. 2B is a block diagram of the LCU processing component 242. The LCU processing component 242 receives LCUs 200 of an input video stream from the coding control component 240 and encodes the LCUs 200 under the control of the coding control component 240 to generate a compressed (encoded) video stream. The LCUs 200 from the coding control component 240 are provided as one input of a motion estimation component (ME) 220, as one input of an intra-prediction estimation component (IPE) 224, and to a positive input of a combiner 202 (e.g., adder or subtractor or the like). Further, although not specifically shown, the prediction mode of each picture as selected by the coding control component 240 is provided to a mode decision component 228 and the entropy coding component 236.

The reference buffer 218 provides reference data to the motion estimation component 220 and to the motion compensation component 222. The reference data may include one or more previously reconstructed and filtered pictures, i.e., reference pictures. A reconstructed picture buffer (not shown) provides reconstructed picture data for the picture currently being encoded to the IPE component 224 and the de-blocking filter component 232.

The motion estimation component 220 provides motion data information to the motion compensation component 222 and the entropy coding component 236. More specifically, the motion estimation component 220 performs tests on CUs in an LCU based on multiple inter-prediction modes (e.g., skip mode, merge mode, and normal or direct inter-prediction), PU sizes, and TU sizes using reference picture data from the reference buffer 218 to choose the best CU partitioning, PU/TU partitioning, inter-prediction modes, motion vectors, etc. based on coding cost, e.g., a rate distortion coding cost. To perform the tests, the motion estimation component 220 may divide an LCU into CUs according to the maximum hierarchical depth of the quadtree, and divide each CU into PUs according to the unit sizes of the inter-prediction modes and into TUs according to the transform unit sizes, and calculate the coding costs for each PU size, prediction mode, and transform unit size for each CU. The motion estimation component 220 provides the motion vector (MV) or vectors and the prediction mode for each PU in the selected CU partitioning to the motion compensation component (MC) 222.

The motion compensation component 222 receives the selected inter-prediction mode and mode-related information from the motion estimation component 220 and generates the inter-predicted CUs. The inter-predicted CUs are provided to the mode decision component 228 along with the selected inter-prediction modes for the inter-predicted PUs and corresponding TU sizes for the selected CU/PU/TU partitioning. The coding costs of the inter-predicted CUs are also provided to the mode decision component 228.

The intra-prediction estimation component (IPE) 224 performs intra-prediction estimation in which tests on CUs in an LCU based on multiple intra-prediction modes, PU sizes, and TU sizes are performed using reconstructed data from previously encoded neighboring CUs stored in the reconstructed picture buffer (not shown) to choose the best CU partitioning, PU/TU partitioning, and intra-prediction modes based on coding cost, e.g., a rate distortion coding cost. To perform the tests, the intra-prediction estimation component 224 may divide an LCU into CUs according to the maximum hierarchical depth of the quadtree, and divide each CU into PUs according to the unit sizes of the intra-prediction modes and into TUs according to the transform unit sizes, and calculate the coding costs for each PU size, prediction mode, and transform unit size for each PU. The intra-prediction estimation component 224 provides the selected intra-prediction modes for the PUs and the corresponding TU sizes for the selected CU partitioning to the intra-prediction component (IP) 226. The coding costs of the intra-predicted CUs are also provided to the intra-prediction component 226.

The intra-prediction component (IP) 226 receives intra-prediction information, e.g., the selected mode or modes for the PU(s), the PU size, etc., from the intra-prediction estimation component 224 and generates the intra-predicted CUs. The intra-predicted CUs are provided to the mode decision component 228 along with the selected intra-prediction modes for the intra-predicted PUs and corresponding TU sizes for the selected CU/PU/TU partitioning. The coding costs of the intra-predicted CUs are also provided to the mode decision component 228.

The mode decision component 228 selects between intra-prediction of a CU and inter-prediction of a CU based on the intra-prediction coding cost of the CU from the intra-prediction component 226, the inter-prediction coding cost of the CU from the motion compensation component 222, and the picture prediction mode provided by the coding control component. Based on the decision as to whether a CU is to be intra-coded or inter-coded, the intra-predicted PUs or inter-predicted PUs are selected. The selected CU/PU/TU partitioning with corresponding modes and other mode related prediction data (if any) such as block vector(s), motion vector(s) and reference picture index (indices) are provided to the entropy coding component 236.

The output of the mode decision component 228, i.e., the predicted PUs, is provided to a negative input of the combiner 202 and to the combiner 238. The associated transform unit size is also provided to the transform component 204. The combiner 202 subtracts a predicted PU from the original PU. Each resulting residual PU is a set of pixel difference values that quantify differences between pixel values of the original PU and the predicted PU. The residual blocks of all the PUs of a CU form a residual CU for further processing.

The transform component 204 performs block transforms on the residual CUs to convert the residual pixel values to transform coefficients and provides the transform coefficients to a quantize component 206. More specifically, the transform component 204 receives the transform unit sizes for the residual CU and applies transforms of the specified sizes to the CU to generate transform coefficients. Further, the quantize component 206 quantizes the transform coefficients based on quantization parameters (QPs) and quantization matrices provided by the coding control component and the transform sizes and provides the quantized transform coefficients to the entropy coding component 236 for coding in the bit stream.

The entropy coding component 236 entropy encodes the relevant data, i.e., syntax elements, output by the various encoding components and the coding control component using context-adaptive binary arithmetic coding (CABAC) to generate the compressed video bit stream. Among the syntax elements that are encoded are picture parameter sets, slice headers, flags indicating the CU/PU/TU partitioning of an LCU, the prediction modes for the CUs, and the quantized transform coefficients for the CUs. The entropy coding component 236 also entropy encodes relevant data from the in-loop filters, such as the SAO parameters.

The LCU processing includes an embedded decoder. As any compliant decoder is expected to reconstruct an image from a compressed bit stream, the embedded decoder provides the same utility to the video encoder. Knowledge of the reconstructed input allows the video encoder to transmit the appropriate residual energy to compose subsequent pictures.

The quantized transform coefficients for each CU are provided to an inverse quantize component (IQ) 212, which outputs a reconstructed version of the transform result from the transform component 204. The dequantized transform coefficients are provided to the inverse transform component (IDCT) 214, which outputs estimated residual information representing a reconstructed version of a residual CU. The inverse transform component 214 receives the transform unit size used to generate the transform coefficients and applies inverse transform(s) of the specified size to the transform coefficients to reconstruct the residual values. The reconstructed residual CU is provided to the combiner 216.

The combiner 216 adds the original predicted CU to the residual CU to generate a reconstructed CU, which becomes part of reconstructed picture data. The reconstructed picture data is stored in the reconstructed picture buffer (not shown) for use by the IPE component 224 and the de-blocking filter component 232.

Various in-loop filters may be applied to the reconstructed picture data to improve the quality of the reference picture data used for encoding/decoding of subsequent pictures. The in-loop filters may include a deblocking filter 232 and a sample adaptive offset filter (SAO) 234. The in-loop filters 232, 234 are applied to each reconstructed LCU in the picture and the final filtered reference picture data is stored in the reference buffer 218.

FIGS. 3A and 3B show block diagrams of an example video decoder, e.g., the video decoder component 112 of FIG. 1, configured to decode bit streams encoded using selective picture-based encryption as described herein during the encoding process. FIG. 3A shows a high level block diagram of the video decoder and FIG. 3B shows a block diagram of the decoding component 342 of the video decoder. In general, the video decoder operates to reverse the encoding operations, i.e., entropy coding, quantization, transformation, and prediction, performed by the video encoder of FIGS. 2A and 2B to regenerate the pictures of the original video stream. In view of the above description of a video encoder, one of ordinary skill in the art will understand the functionality of components of the video decoder without need for detailed explanation.

Referring now to FIG. 3A, the video decoder includes a decoding control component 340, a decoding component 342, a decryption component 344, and a memory 346. The memory 346 may be internal (on-chip) memory, external (off-chip) memory, or a combination thereof. The memory 346 may be used to communicate information between the various components of the video decoder. An input encoded bit stream is provided to the decoding control component 340, e.g., from a source digital system 100 (see FIG. 1). The decoding control component 340 sequences the various operations of the video decoder, i.e., the decoding control component 340 runs the main control loop for video decoding.

For pipelined architectures in which multiple LCUs may be processed concurrently in different components of the decoding component 342, the decoding control component 340 controls the processing of the LCUs by various components of the decoding component 342 in a pipeline fashion. For example, in many embedded systems supporting video processing, there may be one master processor and one or more slave processing modules, e.g., hardware accelerators. The master processor operates as the decoding control component and runs the main control loop for video decoding, and the slave processing modules are employed to off load certain compute-intensive tasks of video decoding such as motion compensation, inverse transformation and inverse quantization, entropy decoding, and loop filtering. The slave processing modules are controlled in a pipeline fashion by the master processor such that the slave processing modules operate on different LCUs of a picture at any given time. That is, the slave processing modules are executed in parallel, each processing its respective LCU while data movement from one processor to another is serial.

Further, the decoding control component 340 performs the processing for decrypting any pictures encrypted using picture-based selective encryption as described herein, passing any pictures to be decrypted to the decryption component 344. More specifically, the decoding control component 340 receives any information needed for decrypting the encrypted pictures including information identifying which pictures are encrypted, and passes the identified encrypted pictures and the decryption information to the decryption component 344. For example, the decoding control component 340 may perform the operations of the method of FIG. 7 as a video stream is decoded. In some embodiments, the selected pictures are decrypted prior to decoding. In some embodiments, the selected pictures are decrypted after decoding.

The decryption component 344 decrypts the encrypted pictures using the appropriate decryption technique, i.e., the decryption technique corresponding to the encryption technique used to encrypt the pictures.

The coding control component 240 also performs processing needed to communicate to a decoder, e.g., the decoder of FIGS. 3A and 3B, receiving the encoded bit stream which of the pictures is encrypted and any other information needed to decrypt the encrypted pictures, e.g., a key or keys for decryption and/or the type of encryption used. This information may be communicated in any suitable way, e.g., in one or more supplemental enhancement information (SEI) messages, in suitable headers and/or parameter sets, etc.

FIG. 3B shows a block diagram of the decoding component 342. The decoding component 342 receives a compressed bit stream from the decoding control component 340 and decodes the encoded pictures. The entropy decoding component 300 receives an entropy encoded (compressed) video bit stream and reverses the entropy encoding using CABAC decoding to recover the encoded syntax elements, e.g., CU, PU, and TU structures of LCUs, quantized transform coefficients for CUs, motion vectors, block vectors, prediction modes, SAO parameters, etc. The decoded syntax elements are passed to the various components of the decoder as needed. For example, decoded prediction modes are provided to the intra-prediction component (IP) 314 or motion compensation component (MC) 310. If the decoded prediction mode is an inter-prediction mode, the entropy decoder 300 reconstructs the motion vector(s) as needed and provides the motion vector(s) to the motion compensation component 310.

The inverse quantize component (IQ) 302 de-quantizes the quantized transform coefficients of the CUs. The inverse transform component 304 transforms the frequency domain data from the inverse quantize component 302 back to the residual CUs. That is, the inverse transform component 304 applies an inverse unit transform, i.e., the inverse of the unit transform used for encoding, to the de-quantized residual coefficients to produce reconstructed residual values of the CUs.

A residual CU supplies one input of the addition component 306. The other input of the addition component 306 comes from the mode switch 308. When an inter-prediction mode is signaled in the encoded video stream, the mode switch 308 selects predicted PUs from the motion compensation component 310 and when an intra-prediction mode is signaled, the mode switch selects predicted PUs from the intra-prediction component 314.

The motion compensation component 310 receives reference data from the reference buffer 312 and applies the motion compensation computed by the encoder and transmitted in the encoded video bit stream to the reference data to generate a predicted PU. That is, the motion compensation component 310 uses the motion vector(s) from the entropy decoder 300 and the reference data to generate a predicted PU.

The intra-prediction component 314 receives reconstructed samples from previously reconstructed PUs of a current picture from the reconstructed picture buffer 320 and performs the intra-prediction computed by the encoder as signaled by an intra-prediction mode transmitted in the encoded video bit stream using the reconstructed samples as needed to generate a predicted PU.

The addition component 306 generates a reconstructed CU by adding the predicted PUs selected by the mode switch 308 and the residual CU. The output of the addition component 306, i.e., the reconstructed CUs, is stored in the reconstructed picture buffer for use by the intra-prediction component 314.

In-loop filters may be applied to reconstructed picture data to improve the quality of the decoded pictures and the quality of the reference picture data used for decoding of subsequent pictures. The applied in-loop filters are the same as those of the encoder, i.e., a deblocking filter 316 and a sample adaptive offset filter (SAO) 318. The in-loop filters may be applied on an LCU-by-LCU basis and the final filtered reference picture data is provided to the reference buffer 312.

Figure 4:
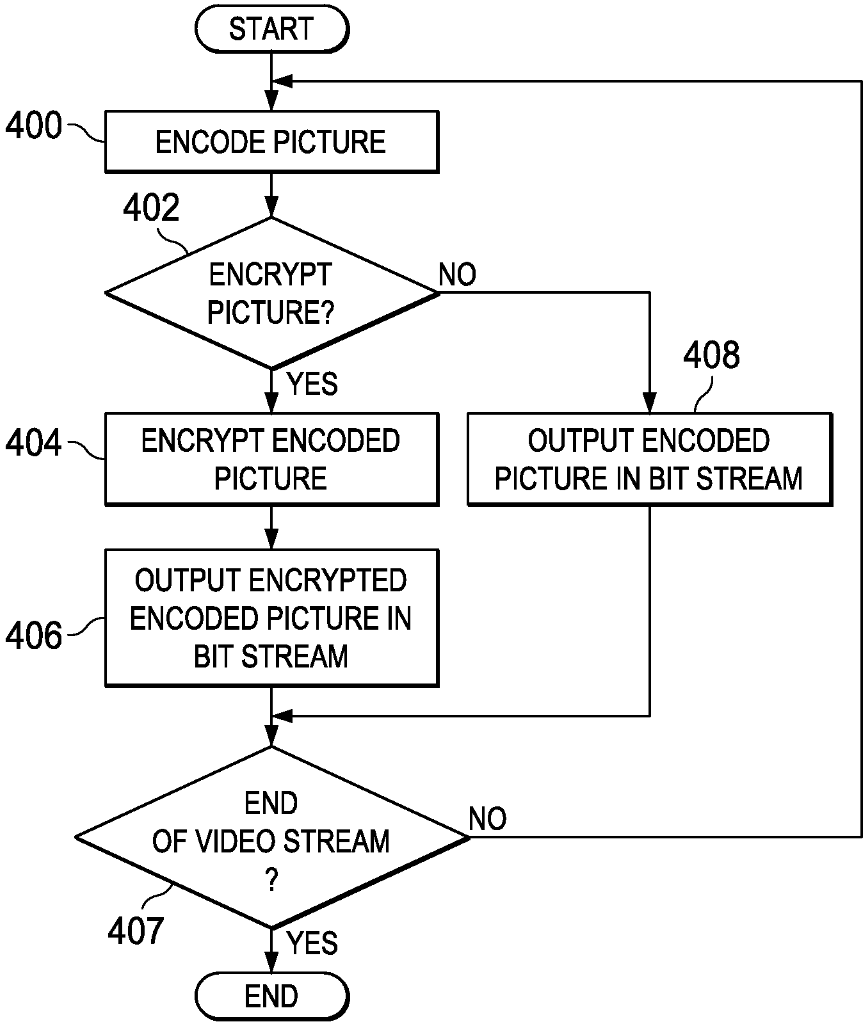
FIGS. 4-7 are flow diagrams of methods.

FIG. 4 is a flow diagram of a method for selective picture-based encryption of a video stream that may be performed by a video encoder, for example, by the encoder of FIGS. 2A and 2B. In general, in this method, pictures are randomly selected for encryption within some constraints. Initially, a picture is encoded 400 by the video encoder. Then, a check 402 is made to determine if the encoded picture is to be encrypted. A method for determining whether or not the current encoded picture is to be encrypted is described in reference to FIG. 5. If the encoded picture is to be encrypted 402, then the encoded picture is encrypted 404 and output 406 into the bit stream. Any suitable encryption technique may be used. Suitable techniques are previously described herein. If the encoded picture is not to be encrypted 402, then the encoded picture is not encrypted and is output 408 into the bit stream. The process continues 407 until the end of the video stream is reached.

Figure 5:
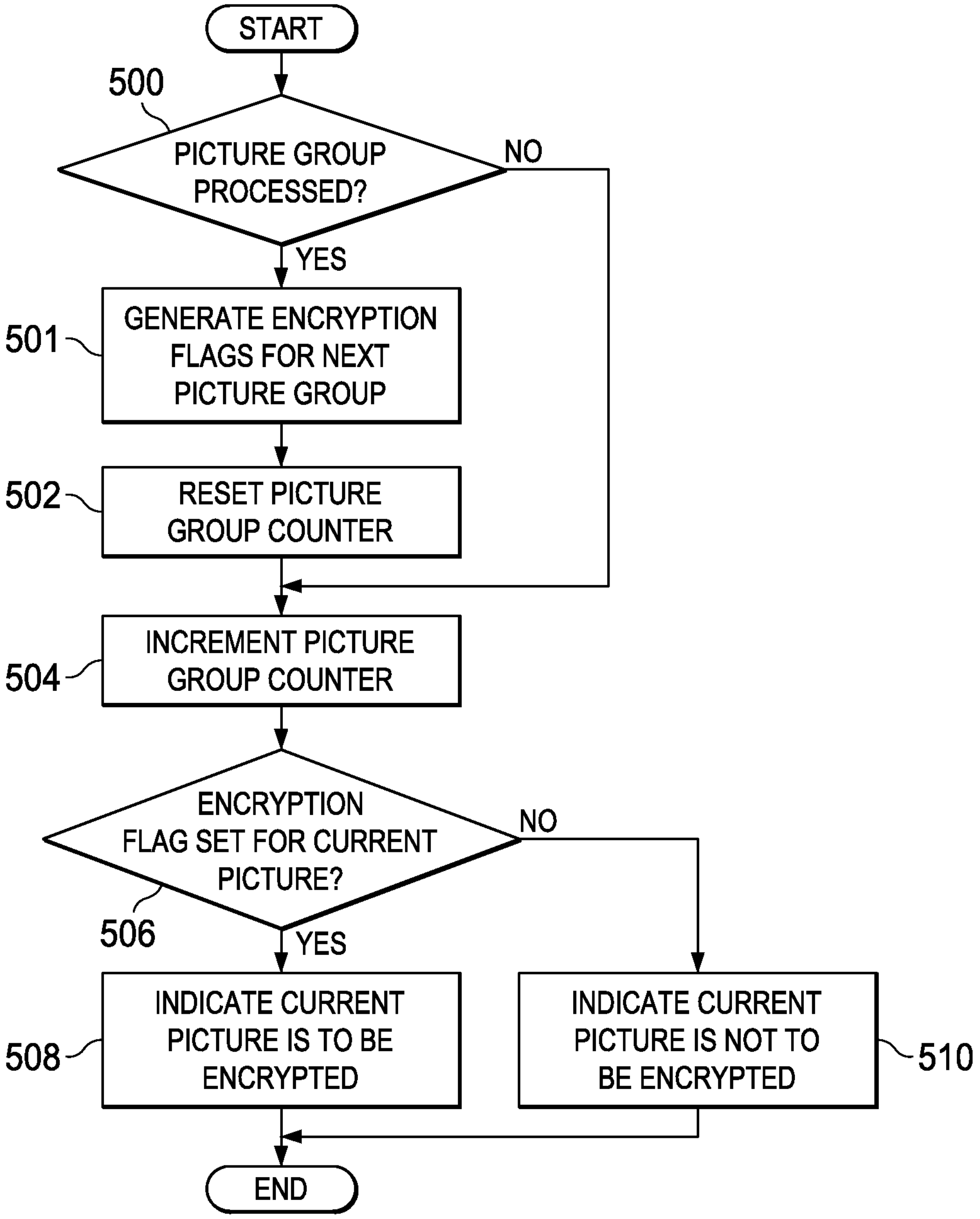

FIG. 5 is a flow diagram of a method for randomly selecting encoded pictures of a video stream for encryption. In this method, the sequential pictures of the video stream are logically divided into sequential groups of sequential pictures referred to herein as picture groups. Any suitable number of sequential pictures may be included in a picture group. In some embodiments, the number of pictures in a picture group is based on the frame rate of the video stream. For example, if the frame rate is 24 frames per second (fps), then the number of pictures in a picture group is 24. In another example, if the frame rate is 30 fps, then the number of pictures in a picture group is 30. A small subset of pictures in a picture group is randomly selected for encryption. Any suitable number of pictures may be included in the encryption subset. In general, the number of pictures in the encryption subset is chosen such that the quality of the decoded video bits stream is substantially corrupted for anyone who does not have the appropriate decryption information. In some embodiments, the number of pictures in this encryption subset may be selected based on the number of pictures in a picture group. In some such embodiments, the number of unencrypted pictures in a picture group is approximately 18. Thus, if the number of pictures in a picture group is 24, the number of pictures in the encryption subset is approximately 6. Similarly, if the number of pictures in a picture group is 30, the number of pictures in the encryption subset is approximately 12.

As shown in FIG. 5, initially a check is made to determine if a complete picture group has been processed 500, e.g., by checking a picture group counter. If a complete picture group has been processed 500, then encryption flags for the next picture group are generated 501 and the picture group counter is reset 502. If a complete picture group has not been processed 500, then the current set of encryption flags is used. There is one encryption flag for each picture in a picture group and these flags are randomly set to indicate which of the pictures in the picture group are to be encrypted, i.e., to identify the subset of pictures in the picture group to be encrypted. A method for generating these encryption flags is described in reference to FIG. 6.

The picture group counter is then incremented 504, and the encryption flag for the current picture is checked 506 to see if the current picture is to be encrypted. If the encryption flag is set for encryption, then an indication that the current picture is to be encrypted is returned 508; otherwise, an indication that the current picture is not to be encrypted is returned 510.

Figure 6:
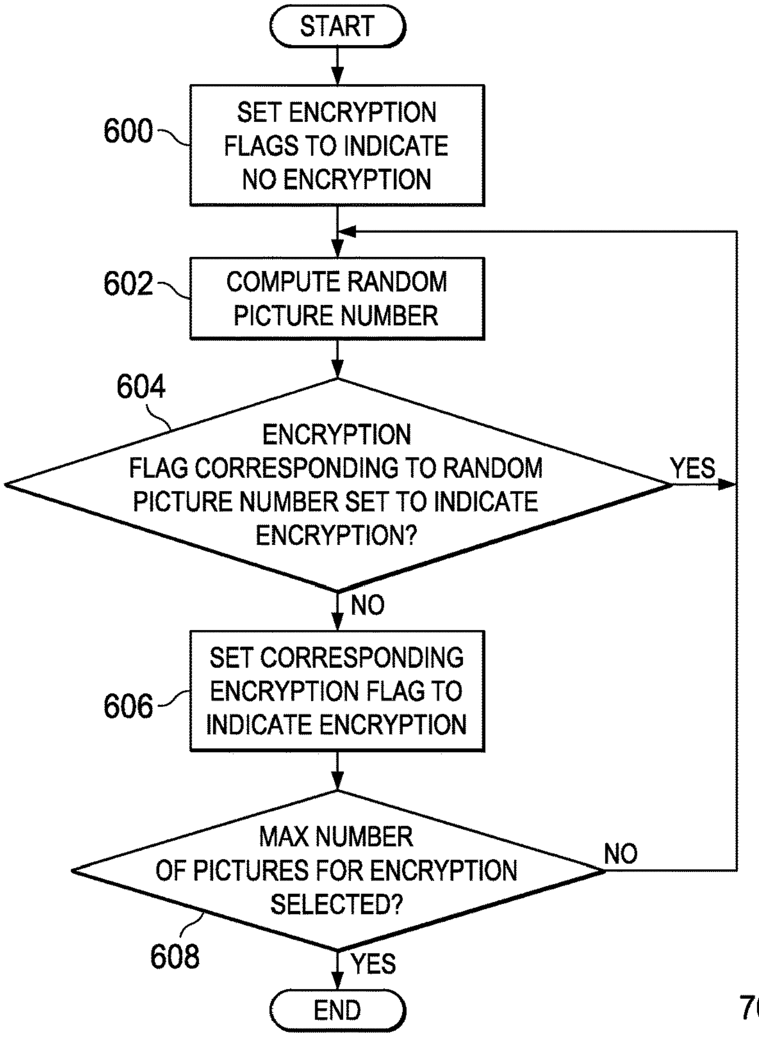

FIG. 6 is a flow diagram of a method for randomly selecting a subset of pictures in a picture group for encryption. Initially, encryption flags, one for each picture in a picture group, are set 600 to indicate no encryption. A random picture number uniquely identifying a picture in the picture group is then computed 602, e.g., by generating a random number and computing the modulo of the random number with the number of pictures in a picture group. If the encryption flag corresponding to the random picture number is not set 604 to indicate encryption, then the encryption flag is set 606 to indicate encryption. If the maximum number of pictures in the picture group that are to be encrypted have been selected 608, then the process terminates; otherwise, the process resumes with step 602. If the encryption flag corresponding to the random picture number is set 604 to indicate encryption, then the process resumes with step 602.

Figure 7:
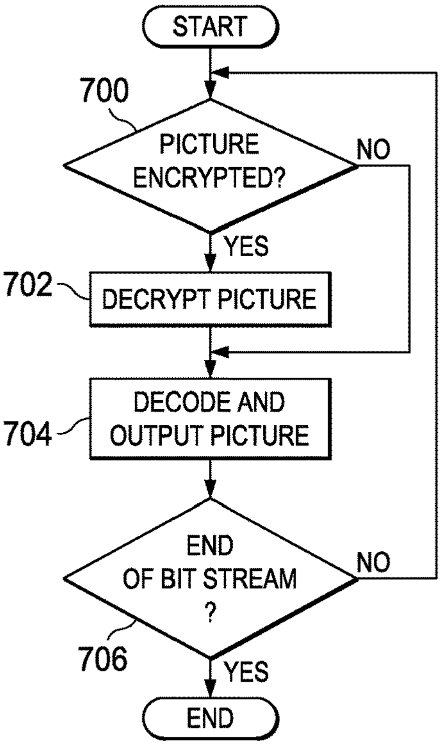

FIG. 7 is a flow diagram of a method for decoding a video bit stream encoded using selective picture-based encryption that may be performed by a video decoder, for example, by the decoder of FIGS. 3A and 3B. The method assumes that information needed for decrypting any encrypted pictures and information identifying which of the pictures is encrypted is communicated to the decoder in a suitable way. As shown in FIG. 7, for each picture in the bit stream, the decoder determines whether or not the picture is encrypted 700. How the decoder makes this determination depends on how the encryption information is signaled. If the current picture is to be decrypted 700, then the encrypted picture is decrypted based on the signaled decryption information, and the decrypted picture is decoded and output 704. If the current picture is not encrypted 700, the picture is decoded and output 704. This process is repeated 706 until the end of the bit stream.

Figure 8:
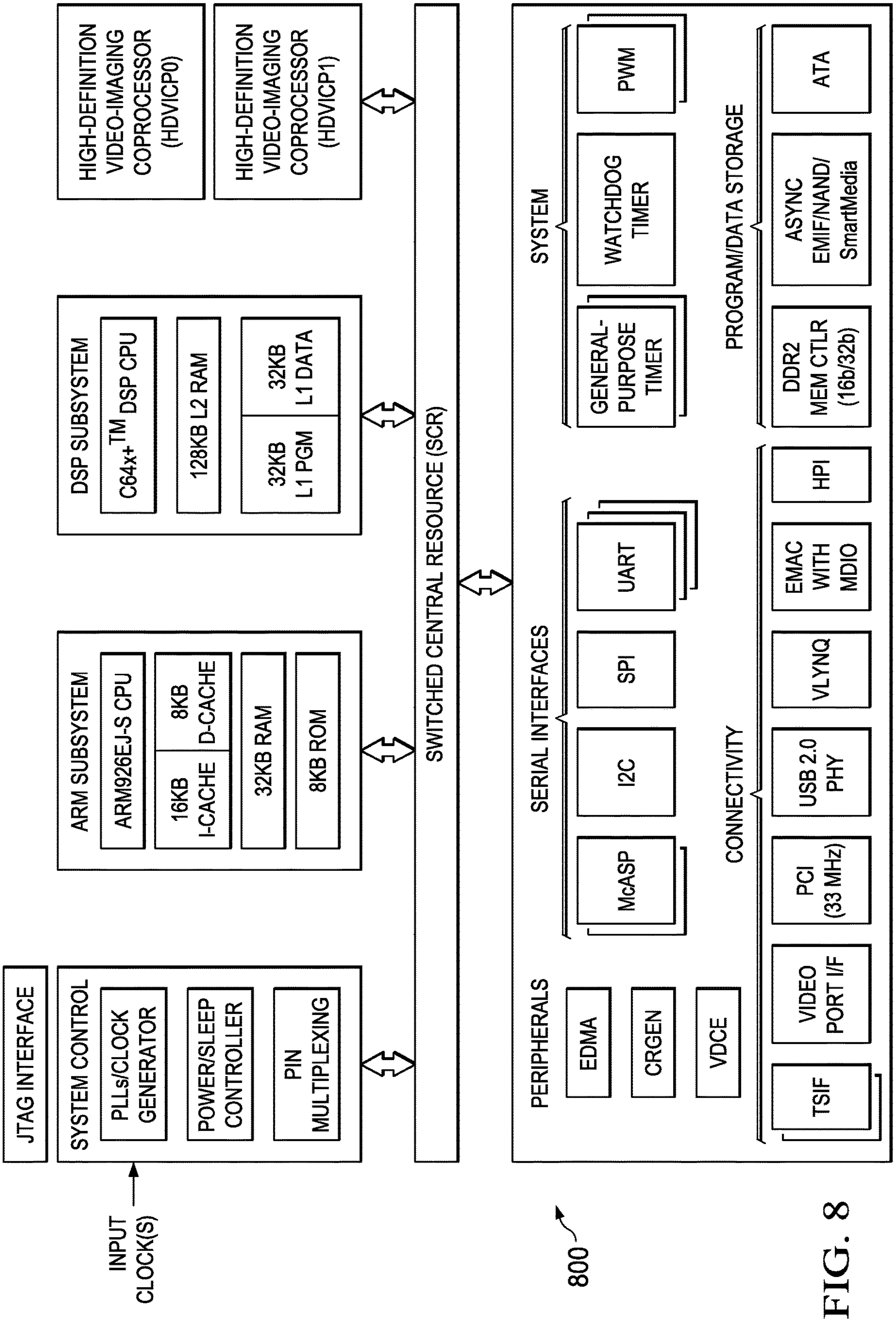
FIG. 8 is a block diagram of an illustrative digital system.

FIG. 8 is a block diagram of an example digital system suitable for use as an embedded system that may be configured to perform selective picture-based encryption as described herein during encoding of a video stream and/or to decrypt pictures encoded using selective picture-based encryption during decoding of a video bit stream as described herein. This example system-on-a-chip (SoC) is representative of one of a family of DaVinci™ Digital Media Processors, available from Texas Instruments, Inc. This SoC is described in more detail in "TMS320DM6467 Digital Media System-on-Chip", SPRS403G, December 2007 or later, which is incorporated by reference herein.

The SoC 800 is a programmable platform designed to meet the processing needs of applications such as video encode/decode/transcode/transrate, video surveillance, video conferencing, set-top box, medical imaging, media server, gaming, digital signage, etc. The SoC 800 provides support for multiple operating systems, multiple user interfaces, and high processing performance through the flexibility of a fully integrated mixed processor solution. The device combines multiple processing cores with shared memory for programmable video and audio processing with a highly-integrated peripheral set on common integrated substrate.

The dual-core architecture of the SoC 800 provides benefits of both DSP and Reduced Instruction Set Computer (RISC) technologies, incorporating a DSP core and an ARM926EJ-S core. The ARM926EJ-S is a 32-bit RISC processor core that performs 32-bit or 16-bit instructions and processes 32-bit, 16-bit, or 8-bit data. The DSP core is a TMS320C64x+TM core with a very-long-instruction-word (VLIW) architecture. In general, the ARM is responsible for configuration and control of the SoC 800, including the DSP Subsystem, the video data conversion engine (VDCE), and a majority of the peripherals and external memories. The switched central resource (SCR) is an interconnect system that provides low-latency connectivity between master peripherals and slave peripherals. The SCR is the decoding, routing, and arbitration logic that enables the connection between multiple masters and slaves that are connected to it.

The SoC 800 also includes application-specific hardware logic, on-chip memory, and additional on-chip peripherals. The peripheral set includes: a configurable video port (Video Port I/F), an Ethernet MAC (EMAC) with a Management Data Input/Output (MDIO) module, a 4-bit transfer/4-bit receive VLYNQ interface, an inter-integrated circuit (I2C) bus interface, multichannel audio serial ports (McASP), general-purpose timers, a watchdog timer, a configurable host port interface (HPI); general-purpose input/output (GPIO) with programmable interrupt/event generation modes, multiplexed with other peripherals, UART interfaces with modern interface signals, pulse width modulators (PWM), an ATA interface, a peripheral component interface (PCI), and external memory interfaces (EMIFA, DDR2). The video port I/F is a receiver and transmitter of video data with two input channels and two output channels that may be configured for standard definition television (SDTV) video data, high definition television (HDTV) video data, and raw video data capture.

As shown in FIG. 8, the SoC 800 includes two high-definition video/imaging coprocessors (HDVICP) and a video data conversion engine (VDCE) to offload many video and image processing tasks from the DSP core. The VDCE supports video frame resizing, anti-aliasing, chrominance signal format conversion, edge padding, color blending, etc. The HDVICP coprocessors are designed to perform computational operations required for video encoding such as motion estimation, motion compensation, intra-prediction, transformation, and quantization. Further, the distinct circuitry in the HDVICP coprocessors that may be used for specific computation operations is designed to operate in a pipeline fashion under the control of the ARM subsystem and/or the DSP subsystem.

As was previously mentioned, the SoC 800 may be configured to perform selective picture-based encryption as described herein during encoding of a video stream and/or to decrypt pictures encoded using selective picture-based encryption during decoding of a video bit stream as described herein. For example, the coding control of the video encoder of FIGS. 2A and 2B may be executed on the DSP subsystem or the ARM subsystem and the computational operations for selecting and encrypting pictures may also be executed on the DSP subsystem or the ARM subsystem. Further, at least some of the computational operations of the LCU processing, including the intra-prediction and inter-prediction of mode selection, transformation, quantization, and entropy encoding may be executed on the HDVICP coprocessors. Similarly, the decoding control of the video decoder of FIGS. 3A and 3B may be executed on the DSP subsystem or the ARM subsystem and the computational operations identifying and decrypting encrypted pictures may also be executed on the DSP subsystem or the ARM subsystem. Further, at least some of the computational operations of the various components of the video decoder, including entropy decoding, inverse quantization, inverse transformation, intra-prediction, and motion compensation may be executed on the HDVICP coprocessors.

Other Embodiments

While the invention has been described with respect to a limited number of embodiments, those skilled in the art, having benefit of this disclosure, will appreciate that other embodiments can be devised which do not depart from the scope of the invention as disclosed herein.

For example, method embodiments have been described herein assuming that pictures are encrypted after encoding and encrypted pictures are decrypted prior to decoding. One of ordinary skill in the art will understand embodiments in which pictures are encrypted prior to encoding and encrypted pictures are decrypted after decoding.

In another example, method embodiments have been described herein in which the number of pictures in a picture group and the number of pictures randomly selected for encryption in a picture group may be static for a video stream. One of ordinary skill in the art will understand embodiments in which the number of pictures in a picture group and the number of randomly selected pictures in a picture group may vary from picture group to picture group in the same video stream. For example, the number of pictures in a picture group and the number of randomly selected pictures may change if the frame rate of the video stream changes.

Embodiments of the methods, encoders, and decoders described herein may be implemented in hardware, software, firmware, or any combination thereof. If completely or partially implemented in software, the software may be executed in one or more processors, such as a microprocessor, application specific integrated circuit (ASIC), field programmable gate array (FPGA), or digital signal processor (DSP). The software instructions may be initially stored in a computer-readable medium and loaded and executed in the processor. In some cases, the software instructions may also be sold in a computer program product, which includes the computer-readable medium and packaging materials for the computer-readable medium. In some cases, the software instructions may be distributed via removable computer readable media, via a transmission path from computer readable media on another digital system, etc. Examples of computer-readable media include non-writable storage media such as read-only memory devices, writable storage media such as disks, flash memory, memory, or a combination thereof.

Although method steps may be presented and described herein in a sequential fashion, one or more of the steps shown in the figures and described herein may be performed concurrently, may be combined, and/or may be performed in a different order than the order shown in the figures and/or described herein. Accordingly, embodiments should not be considered limited to the specific ordering of steps shown in the figures and/or described herein.

It is therefore contemplated that the appended claims will cover any such modifications of the embodiments as fall within the true scope of the invention.

What is claimed is:

1. A method comprising:
receiving, by a video encoder, the video stream;
dividing, by the video encoder, the video stream into at least a group of sequential pictures;
determining, by the video encoder, if the group of sequential pictures has been processed based on a picture group counter;
in response to determining that the group of sequential pictures has not been processed:
clearing an encryption flag for each picture in the group of sequential pictures;
randomly selecting, by the video encoder, a number of pictures from the group of sequential pictures, the number of pictures selected from the group of sequential pictures is based on the number of sequential pictures in the group of sequential pictures;
setting, by the video encoder, the respective encryption flag for each randomly selected picture; and
encrypting, by the video encoder, the randomly selected pictures from the group of sequential pictures based on the respective encryption flag for the picture being set.

2. The method of claim 1, wherein a number of pictures in the group of sequential pictures is based on a frame rate of the video stream.

3. The method of claim 1, wherein the group of sequential pictures has 24 pictures, and the number of pictures selected is 6.

4. The method of claim 1, wherein the group of sequential pictures has 30 pictures, and the number of pictures selected is 12.

5. The method of claim 1, wherein each picture of the randomly selected pictures is encrypted after the picture is encoded.

6. The method of claim 1, wherein each picture of the randomly selected pictures is encrypted before the picture is encoded.

7. A video encoder comprising:
one or more microprocessors configured to:
receive the video stream;
divide the video stream into at least a group of sequential pictures;
determining, by the video encoder, if the group of sequential pictures has been processed based on a picture group counter;
in response to determining that the group of sequential pictures has not been processed:
clear an encryption flag for each picture in the group of sequential pictures;
randomly select a number of pictures from the group of sequential pictures, the number of pictures selected from the group of sequential pictures is based on the number of sequential pictures in the group of sequential pictures;
set the respective encryption flag for each randomly selected picture; and
encrypt the randomly selected pictures from the group of sequential pictures based on the respective encryption flag for the picture being set.

8. The apparatus of claim 7, wherein a number of pictures in the group of sequential pictures is based on a frame rate of the video stream.

9. The apparatus of claim 7, wherein the group of sequential pictures has 24 pictures, and the number of pictures selected is 6.

10. The apparatus of claim 7, wherein the group of sequential pictures has 30 pictures, and the number of pictures selected is 12.

11. The apparatus of claim 7, wherein each picture of the randomly selected pictures is encrypted after the picture is encoded.

12. The apparatus of claim 7, wherein each picture of the randomly selected pictures is encrypted before the picture is encoded.

13. A non-transitory computer-readable medium comprising instructions that, when executed by a video encoder, cause the video encoder to:
divide a video stream into a at least a group of sequential pictures;
determining, by the video encoder, if the group of sequential pictures has been processed based on a picture group counter;
in response to determining that the group of sequential pictures has not been processed:
clearing an encryption flag for each picture in the group of sequential pictures;
randomly select a number of pictures from the group of sequential pictures, the number of pictures selected from the group of sequential pictures is based on the number of sequential pictures in the group of sequential pictures;
set the respective encryption flag for each randomly selected picture; and
encrypt the randomly selected pictures from the group of sequential pictures responsive to the encryption flag for the pictures being set as the video stream is encoded.

* * * * *